United States Patent [19]

Gil

[11] 4,119,092
[45] Oct. 10, 1978

[54] METHODS OF REDUCTION OF BONE FRACTURES

[76] Inventor: José-Luis Gil, Avda. Principado de Andorra, 3, Tarragona, Spain

[21] Appl. No.: 789,831

[22] Filed: Apr. 22, 1977

[51] Int. Cl.² .......................... A61F 5/04; A61B 17/18
[52] U.S. Cl. ............................... 128/92 D; 128/92 E; 128/92 EB
[58] Field of Search ............... 128/92 D, 92 R, 92 E, 128/92 EB, 92 G, 84 R

[56] References Cited

U.S. PATENT DOCUMENTS

| 2,494,229 | 1/1950 | Collison | 128/92 R |
| 3,866,607 | 2/1975 | Forsythe et al. | 128/92 D X |
| 3,900,025 | 8/1975 | Barnes, Jr. | 128/92 D |

FOREIGN PATENT DOCUMENTS

| 378,516 | 1/1964 | Switzerland | 128/92 D |
| 1,173,480 | 12/1969 | United Kingdom | 128/92 D |

Primary Examiner—Ronald L. Frinks

[57] ABSTRACT

A method of reduction of bone fractures is described wherein two segments of a broken bone are drawn together by means of a plate extending across both segments, securing one end of the plate to one segment of bone, securing the other side of the plate through a slot in the plate to the other segment of bone, and applying a tool having a pinion engaging another slot in the plate provided with a rack, a pin on the end of the tool engaging a hole in the bone, so that upon rotation of the tool the two segments of bone are drawn together. A jig for drilling the necessary holes for securing the segments is also described.

3 Claims, 5 Drawing Figures

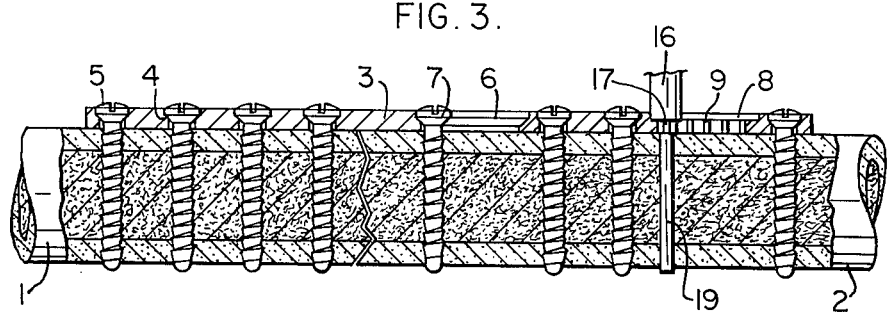
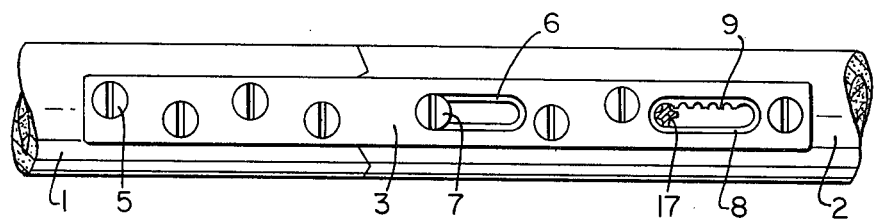
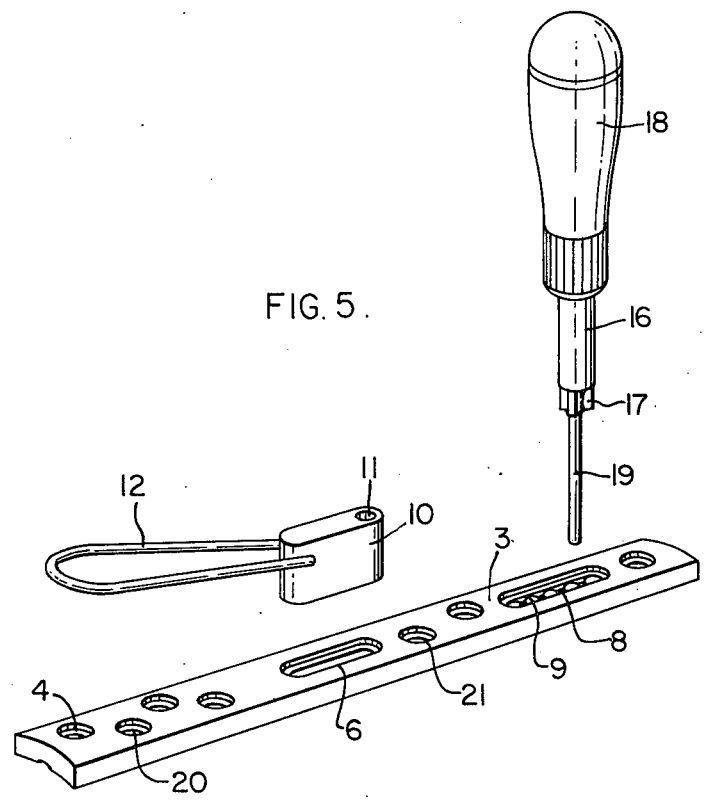

METHODS OF REDUCTION OF BONE FRACTURES

BACKGROUND

The present invention relates to improvements in the methods used for the reduction of bone fractures, especially fractures of the long bones such as those of the upper and lower extremities of man.

Systems for the treatment of bone fractures have long best known, which consist in securing the position of the two piece into which a bone, especially one of the long type, has been broken, by placing a metal plate astride both of the segments, precisely in the contact zone of same, the said plate being fastened by means of screws inserted into openings made with a drill and bit. For the installation of the plate it is necessary first to place the two segments of the bone in the normal position of the latter, bringing together the two matching ends which the fracture produced, so that, they become reunited by recalcification, the strength of the bond will be recovered, with the implanted plate contributing thereto.

The practice of the above method requires, of course, the progressive advancement of the segments of the bone from the position in which they were situated when the reduction of the fracture was started to position moment in which the apposite portions of the segments are in contact. the said operation of putting these segments in contact and alignment can prove to be laborious when the fracture is accompanied by an effect of percussion, flexion, torsion or injury on the extremity, which can considerably complicate the operation of aligning and joining the segments of the bone which it is desired to rejoin.

THE INVENTION

The improvements which are the object of this invention are aimed at eliminating or at least substantially reducing the difficulties described above, by furnishing the traumatologist with means to facilitate the reduction of a fracture, even in cases in which the segments of a bone are greatly separated. With the practice of the improvements in question, a progressive and sure apposition of the pieces is obtained, the fixation of the healing position, and the likewise reliable fixation of an auxiliary plate to immobilize the bone segments against one another.

To facilitate the explanation of the invention, the present specification is accompanied by drawings in which an embodiment of improvements in methods of reduction of bone fractures is shown by way of non-restrictive example, on the basis of the principles set forth in the claims.

In these drawings,

FIGS. 3 and 4 show the two segments of the broken bone now joined together at the location of the fracture and the use of the material elements which have facilitated the reduction of the said segments.

FIG. 5 is a perspective drawing of the metal plate incorporated into the bone, a tool which produces the displacement of one of the segments of the bone, and an auxiliary tool which facilitates the drilling of holes.

Figure 1:
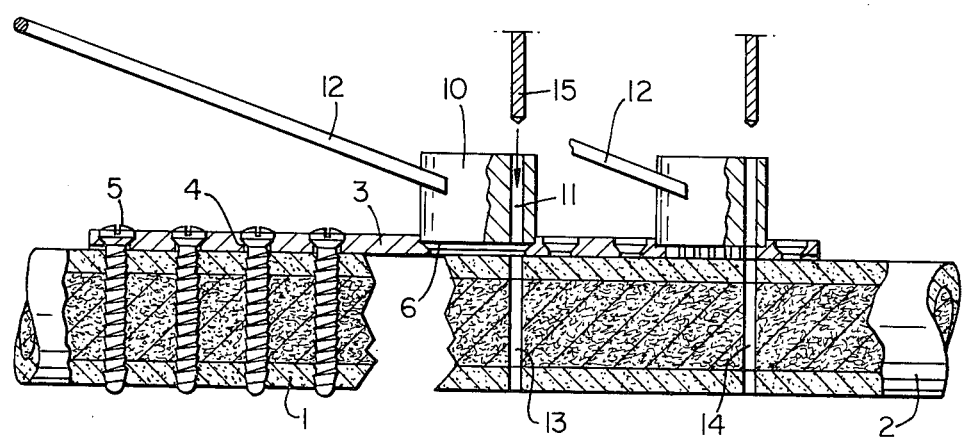
FIG. 1 shows a long bone of an extremity of the human body and the incorporation of a metal plate which will contribute to the healing thereof.
Figure 2:
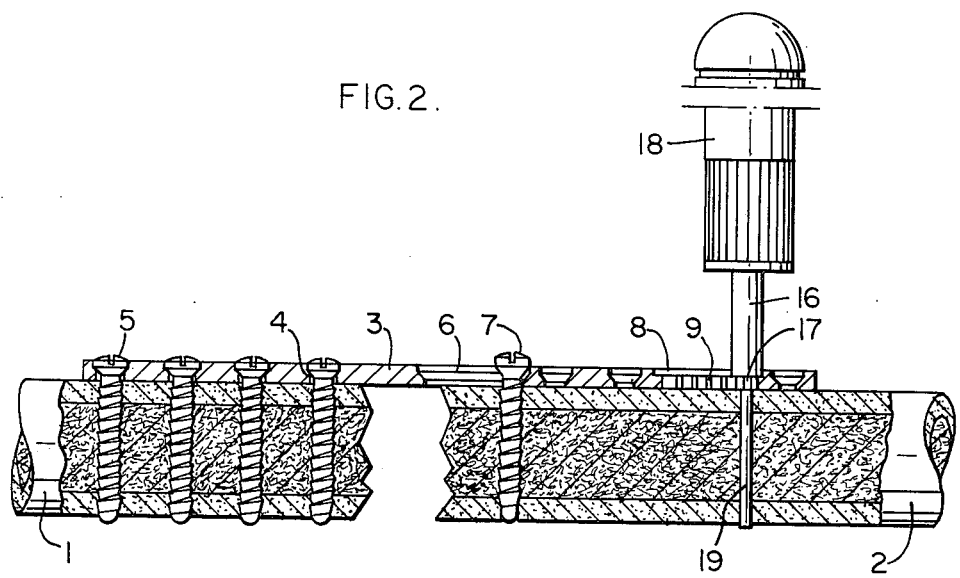
FIG. 2 shows the use of one of the material elements which permit the practice of the present improvements in methods for the reduction of the fracture.

The numerals in the drawings correspond to the following parts: 1 and 2, segments of a broken bone corresponding to an extremity of the human body, which have been represented, for the sake of simplicity and clarity, as a tubular structure of uniform diameter; 3, a metal plate with apertures 4, which is made of a special stainless steel alloy that is incorporated into the bone, and which are different from the known plates used for this purpose in ways which bring about the improvements to be described; 5, special screw inserted into one of the forward chamfered apertures and threaded into the cortical bone or proximal (near) wall and distal (far) wall of one of the segments of the bone, in the manner seen in the first three figures; 6, chamfered slot longitudinally disposed on plate 1, into which there is inserted a screw 7 applied precisely to the bone segment other than the one that received the first screw 5, which is situated at the left end of the plate 3 as seen in the same figures; 8, a slot similar to slot 6, in which the teeth 9 are seen in one of its inside walls, in the manner of a rack; 10, an auxiliary piece in the form of a block whose bottom has a cross sectional shape similar to the orifices of the apertures 6 and 8, in which it can be temporarily fitted in the manner indicated in FIG. 1, the through bore 11 thereof serving as a guide for the introduction of the bit 15 of a drill for drilling the holes 13 and 14 in the walls of the bone; 12, a handle for holding the block 10; 16, a tool of cylindrical shape bearing the pinion 17 whose teeth correspond to those of the rack 9, and having the handle 18 and the prolongation 19 for its manipulation and insertion into the hole 14 in the bone.

The practice of the method described, with the improvements contemplated in the present invention, can be understood readily from the drawings, it being seen that, after the insertion of a first screw 5 into one of the segments 1 of the broken bone, and the insertion of another screw 7 in the other segment 2 of the same bone, the rotation of the tool 16 inserted into the hole 14 in the bone, will, by the rotation of the pinion and its engagement with the rack, produce the displacement of the segment 2 of the bone, which will approach segment 1 until the two are in contact, as shown in FIG. 3, at which time the screw 7 will have moved within the slot 6 by a distance approximately equal to the distance which existed between the two bone segments before they were drawn together. The screw is tightened to hold it in place, and when this has been accomplished, the rest of the holes are drilled into the proximal and distal cortical bone substance and the corresponding screws are installed, thereby completing the installation of the auxiliary plate.

It can be seen, therefore, that the traumatologist can succeed in bringing the two segments of the broken bone together and hold them in contact with much greater ease, and hold them immobile during the operation of drilling the holes 20 and 21 into which he will successively place the screws to hold the plate 3. Obviously, this plate can be made in a variety of shapes with different numbers of apertures and bores.

Everything that does not affect, alter, change or modify the essence of the improvements described shall be variable to the effects of the present invention.

The following are claimed as the subject matter of this invention:

1. Improvements in methods of reduction of bone fractures, especially those which make use of a longitudinal plate of an oxidation resistant metal placed along the broken bone with its halves in contact with the ends of the segments thereof and with apertures for the insertion of screws into the proximal and distal cortical bone substance, comprising bringing together the two bone segments by first fastening one of the ends of the longitudinal plate to one of the segments then fastening the central portion of the same plate to the other segment through a slot provided in the said central portion thereof, said plate being further provided with a second slot having teeth on its internal side wall, forming a rack, said second slot being situated adjacent one of the ends of said plate, and progressively bringing together the two segments of the broken bone until they are placed in contact and alignment for the purpose of their relative immobilization for their further mending, by displacement of the said other bone segment with respect to said plate by the action of a tool applied to the slot situated adjacent the end of said plate and bearing a lateral pinion cooperating with the internal rack toothing of said second slot.

2. A method according to claim 1 wherein the tool used to obtain the displacement of said other bone segment comprises an upper operating handle on a cylindrical body, said body being provided at its lower portion with a plurality of teeth disposed in the manner of a pinion of a pitch equivalent to that of the rack formed in the said second slot in said plate, and, at the end corresponding to the pinion, terminating in a pin designed for introduction into a hole previously drilled in each of the cortical walls of said other bone segment.

3. A method according to claim 2 wherein holes are drilled in the walls of the bone for the insertion of diametrically fitted screws with their heads inserted into chamfered apertures in said plate with the aid of a block whose bottom has a shape equivalent to that of said chamfered apertures provided on the outer portion of each of the slots in said plate, a transverse bore being provided in said block to serve as a guide for the bit of a drilling tool applied in a direction perpendicular to the axis of each of the bone segments to be joined, the said block having a handle for positioning and retaining the same in place.

* * * * *